United States Patent
Billich et al.

(10) Patent No.: US 7,795,251 B2
(45) Date of Patent: *Sep. 14, 2010

(54) 3,4-DIHYDRO-BENZO[E][1,3]OXAZIN-2-ONES

(75) Inventors: Andreas Billich, Vienna (AT); Hubert Gstach, Vienna (AT); Philipp Lehr, Vienna (AT)

(73) Assignee: Novartis AG, Basel (CH)

( * ) Notice: Subject to any disclaimer, the term of this patent is extended or adjusted under 35 U.S.C. 154(b) by 22 days.

This patent is subject to a terminal disclaimer.

(21) Appl. No.: 11/911,154

(22) PCT Filed: Apr. 13, 2006

(86) PCT No.: PCT/EP2006/003445

§ 371 (c)(1),
(2), (4) Date: Jun. 10, 2008

(87) PCT Pub. No.: WO2006/108671

PCT Pub. Date: Oct. 19, 2006

(65) Prior Publication Data

US 2009/0156588 A1   Jun. 18, 2009

(30) Foreign Application Priority Data

Apr. 15, 2005  (GB)  ................. 0507695.5

(51) Int. Cl.
*A61K 31/535*  (2006.01)
*C07D 265/12*  (2006.01)
*C07D 498/00*  (2006.01)

(52) U.S. Cl. ................ 514/229.5; 544/89; 544/97

(58) Field of Classification Search .......... 514/229.5; 544/89, 97

See application file for complete search history.

(56) References Cited

U.S. PATENT DOCUMENTS 4,499,066 A * 2/1985 Moro et al. .............. 424/465

OTHER PUBLICATIONS

Takai, Haruki et al., "Synthesis and Pharmacological Evaluation of Piperidine Derivatives with Various Heterocyclic Rings at the 4-Position", Chemical & Pharmaceutical Bulletin, 33(3)1104-1115(1985).
Kemp, Daniel S. et al., "The Chemistry of Acylsalicylamides. I. Base-Catalyzed Decomposition of o-benzyloxycarbonylglycyl-n-ethylsalicylamide", Journal of Organic Chemistry, 36(1)157-161(1971).
Sterba, Vojeslav et al., "The Base-Catalysed Cyclisation of Phenyl N-(2-hydroxybenzyl)-N- methylcarbamates is Concerted", Organic & Biomolecular Chemistry, 1(2)415-421(2003).
Yadav, Lal Dhar S. et al., "Novel Salicylaldehyde-Based Mineral-Supported Expeditious Synthesis of Benzoxazin-2-ones", Journal of Organic Chemistry, 69(23)8118-8120(2004).
Mindl, Jaromir et al., "Cyclization of Substituted phenyl N-(2-hydroxybenzyl) carbamates in aprotic solvents. Synthesis of 4H-1,3-benzoxazin-2(3H)-ones", Collection of Czechoslovak Chemical Communications, 65(8)1262-1272 (2000).
Capuano, Lilly et al., "New Method of Nucleophilic Substitution by Exchange of the Carbomoyloxy Group", Chemische Berichte, 103(11)3459-3469(1970), English Abstract.
Kornet, Milton J., "Synthesis and Anticonvulsant Activity of 3-alkyl-3,4-dihydro-2(1H)-quinazolinones", Journal of Heterocyclic Chemistry, 29(103)103-105(1992).
De Angelis, L., "Coroxazone", Drugs of Today, 12(6)235-237(1976).

* cited by examiner

*Primary Examiner*—Sreeni Padmanabhan
*Assistant Examiner*—Sarah Pihonak
(74) *Attorney, Agent, or Firm*—John Alexander

(57) ABSTRACT

The present invention relates 3,4-dihydro-benzo[e][1,3]oxazin-2-ones which are substituted at the nitrogen atom by unsubstituted or substituted $(C_{1-8})$alkyl, $(C_{3-8})$cycloalkyl, $(C_{3-8})$cycloalkyl$(C_{1-4})$alkyl, $(C_{6-18})$aryl or $(C_{6-18})$aryl$(C_{1-4})$alkyl and their use as pharmaceuticals.

6 Claims, No Drawings

3,4-DIHYDRO-BENZO[E][1,3]OXAZIN-2-ONES

This application is the National Stage of Application No. PCT/EP2006/003445, filed on Apr. 13, 2006, which claims priority to Great Britain Application No. 0507695.5, filed on Apr. 15, 2005, the contents of which are incorporated herein by reference in their entirety.

The present invention relates 3,4-dihydro-benzo[e][1,3] oxazin-2-ones, e.g. which are mediators of human macrophage migration inhibitory factor (MIF) activity.

MIF is a cytokine with a wide variety of cellular and biological activities (see e.g. Orita at al., Curr. Pharm. Design 8:1297-1317, 2002; Nishihira, J Interferon Cytokine Res 20:751-762, 2000; Swope & Lolis, Rev. Physiol. Biochem. Pharmacol. 139:1-32, 1999; Metz & Bucala, Adv. Immunol. 66:197-223, 1997; and Bucala, FASEB J. 14:1607-1613, 1996). The three-dimensional crystal structure of human MIF reveals that the protein exists as a homotrimer (see e.g. Lolis et al., Proc. Ass. Am. Phys. 108:415-419, 1996).

MIF was found to inhibit the random migration of macrophages, and to be associated with delayed-type hypersensitivity reactions (see e.g. George & Vaughan, Proc. Soc. Exp. Biol. Med. 111:514-521, 1962; Weiser et al., J. Immunol. 126:1958-1962, 1981; Bloom & Bennett, Science, 153:80-82, 1966; David, Proc. Natl. Acad. Sci. USA 56:72-77, 1966). MIF was also shown to enhance macrophage adherence, phagocytosis and tumoricidal activity (see e.g. Nathan et al., J. Exp. Med. 137:275-288, 1973; Nathan et al., J. Exp. Med. 133:1356-1376, 1971; Churchill et al., J. Immunol. 115:781-785, 1975).

Recombinant human MIF was originally cloned from a human T cell library (see e.g. Weiser et al., Proc. Natl. Acad. Sci. USA 86: 7522-7526, 1989), and was shown to activate blood-derived macrophages to kill intracellular parasites and tumor cells in vitro, to stimulate IL-1β and TNFα expression, and to induce nitric oxide synthesis (see e.g. Weiser et al., J. Immunol. 147:2006-2011, 1991; Pozzi et al., Cellular Immunol. 145:372-379, 1992; Weiser et al., Proc. Natl. Acad. Sci. USA 89:8049-8052, 1992; Cunha et al., J. Immunol. 150: 1908-1912, 1993).

More recently it has been found that MIF is not only a cytokine product of the immune system, but also is a hormone-like product of the endocrine system, particularly the pituitary gland. This work has underscored the potent activity of MIF as a counter-regulator of the anti-inflammatory effects of the glucocorticoids (both those endogenously released and those therapeutically administered), with the effect that the normal activities of glucocorticoids to limit and suppress the severity of inflammatory responses are inhibited by MIF and the endogenous MIF response may thus seen as a cause or an exacerbative factor in a variety of inflammatory diseases and conditions (see e.g. Donnelly and Bucala, Molecular Medicine Today 3:502-507, 1997).

MIF is now known to have several biological functions beyond its association with delayed-type hypersensitivity reactions. For example, MIF released by macrophages and T cells acts as a pituitary mediator in response to physiological concentrations of glucocorticoids (see e.g. Bucala, FASEB J. 14:1607-1613, 1996). This leads to an overriding effect of glucocorticoid immunosuppressive activity through alterations in TNF-α, IL-β, IL-6, and IL-8 levels. Additional biological activities include the regulation of stimulated T cells (see e.g. Bacher et al., Proc. Natl. Acad. Sci. USA 93:7849-7854, 1996), the control of IgE synthesis (see e.g. Mikayama et al., Proc. Natl. Acad. Sci. USA 90:10056-60, 1993), the functional inactivation of the p53 tumor suppressor protein (see e.g. Hudson et al., J. Exp. Med. 190:1375-1382, 1999), the regulation of glucose and carbohydrate metabolism (see e.g. Sakaue et al., Mol. Med. 5:361-371, 1999), and the regulation of tumor cell growth and of angiogenesis (see e.g. Chesney et al., Mol Med. 5:181-191, 1999; Shimizu et al., Biochem. Biophys. Res. Commun. 264:751-758, 1999; Mitchell & Bucala, Cancer Biol. 10:359-366, 2000). A role of MIF in atherogenesis (see e.g. Lin et al., Circulation Res. 8:1202-1208, 2000), in asthma (see e.g. Yamaguchi et al., Clin. Exp. Allergy 30:1244-1249, 2000), and in malaria (see e.g. Martiney et al., Infection Immunity 68:2259-2267, 2000) has also been implicated.

Anti-MIF antibodies have been shown to be active in a variety of models: endotoxin- and exotoxin-induced toxic shock (see e.g. Bernhagen et al., Nature, 365:756-759, 1993; Kobayashi et al., Hepatology, 29:1752-1759, 1999; Calandra et al., Proc. Natl. Acad. Sci. USA., 95:11383-11388, 1998; Makita et al., Am. J. Respir. Crit. Care Med. 158:573-579, 1998, Calandra et al., Nat. Med. 6:164-170, 2000), T-cell activation (see e.g. Bacher et al., Proc. Natl. Acad. Sci. USA. 93:7849-7854, 1996), autoimmune diseases, including rheumatoid arthritis (see e.g. Leech et al., Arthritis Rheum., 42:1601-1608, 1999), uveoretinitis (see e.g. Kitaichi et al., Curr. Eye Res., 20:109-114, 2000), glomerulonephritis (see e.g. Yang et al. Mol. Med. 4: 413-424, 1998), colitis (see e.g. de Jong et al., Nat. Immunol. 2:1061-1066, 2001; Ohkawara et al., Gastroenterol. 123: 256-270, 2002), multiple sclerosis (see e.g. Denkinger et al., J Immunol. 170:1274-82, 2003), atherosclerosis (see e.g. Burger-Kentischer et al. Atherosclerosis. 184:28-38, 2006) and skin graft destruction (see e.g. Hou et al., Transplantation 72: 1890-1897, 2001). Furthermore, anti-MIF antibodies have been shown to inhibit tumor growth and angiogenesis (see e.g. Chesney et al., Mol. Med. 5:181-191, 1999; Ogawa et al., Cytokine 12:309-314, 2000; Mitchell & Bucala, Cancer Biol. 10:359-366, 2000). Based on the activity of the anti-MIF antibodies, the therapeutic potential of low molecular weight MIF-inhibitors is high.

MIF shares significant sequence homology (36% identity) with D-dopachrome tautomerase, and has enzymatic activity to catalyze the tautomerization of the non-physiological substrates D-dopachrome (see e.g. Rosengren et al., Mol. Med. 2:143-149, 1996) and L-dopachrome methyl ester (see e.g. Bendrat et al., Biochemistry, 36:15356-15362, 1997) (FIG. 1A). Additionally, phenylpyruvic acid and p-hydroxyphenylpyruvic acid (see e.g. Rosengren et al., FEBS Letter, 417: 85-88, 1997), and 3,4-dihydroxyphenylaminechrome and norepinephrinechrome (see e.g. Matsunaga et al., J. Biol. Chem., 274:3268-3271, 1999) are MIF substrates. Various inhibitors of the MIF tautomerase activity have been described (see e.g. Orita et al. J. Med. Chem. 44:540-547, 2001; Senter et al., Proc. Natl. Acad. Sci (USA) 99:144-149, 2002; Dios et al., J. Med. Chem. 45: 2410-2416, 2002).

It was now surprisingly found that a certain class of compounds is mediating MIF-activity, e.g. inhibiting MIF activity by inhibition of the tautomerase activity of MIF.

In one aspect the present invention provides a compound of formula

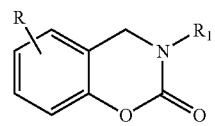

I wherein R is hydrogen, or one or more, e.g. one, hydroxy, mercapto, $SR_3$, $OR_3$, or halogen, $R_1$ is an aliphatic or arylic, optionally heterocyclic, group comprising in case of a non-heterocyclic group at least 6, e.g. 6 to 24 carbon atoms, and comprising in case of a heterocyclic group at least 6 ring members, e.g. 6 to 24, e.g. wherein the heterocyclic group includes a fused heterocyclic ring (system), e.g. a ring (system) wherein another ring is anellated to heterocyclyl, and comprising 1 to 6 heteroatoms selected from N, O, S;

e.g. $R_1$ is preferably an aliphatic or arylic group comprising 6 to 24 carbon atoms and comprising a cyclic group, e.g. including unsubstituted or substituted
- $(C_{6-22})$alkyl, $(C_{6-22})$alkenyl or $(C_{6-22})$alkinyl, e.g. n-hexyl,
- $(C_{6-12})$cycloalkyl$(C_{0-4})$alkyl, e.g. cyclohexyl,
- $(C_{6-18})$aryl$(C_{0-4})$alkyl, e.g. including phenyl, naphthyl, biphenylyl, benzyl,
- $(C_{6-12})$cycloalkyl$(C_{0-4})$alkyl or $(C_{6-12})$aryl$(C_{0-4})$alkyl wherein cycloalkyl or aryl is optionally anellated or fused with another ring (system), such as anellated or fused with an aliphatic ring (system) or an aliphatic or aromatic heterocyclic ring (system), wherein fused or anellated aryl or cycloalkyl comprises 6 to 24 ring members, and wherein heterocyclyl comprises 1 to 4 heteroatoms, selected from S, O, N; e.g. aryl fused or anellated with a crown ether,
- heterocyclyl$(C_{0-4})$alkyl, wherein heterocyclyl is optionally anellated or fused with another ring (system), e.g. including aromatic and aliphatic heterocyclyl having 3 to 18 ring members and 1 to 4 heteroatoms selected from N, O, S;

and $R_3$ an aliphatic or aromatic, optionally heterocyclic group comprising 1 to 16 carbon atoms, such as 1 to 12 carbon atoms, and in case of $OR_3$ in the meaning of R, $R_3$ is additionally $NH_2SO_2$, e.g. wherein an aliphatic or aromatic, optionally heterocyclic group includes unsubstituted or substituted
- $(C_{1-8})$alkyl, $(C_{2-8})$alkenyl or $(C_{2-8})$alkinyl, e.g. methyl,
- $(C_{3-12})$cycloalkyl$(C_{0-4})$alkyl,
- $(C_{6-12})$aryl$(C_{0-4})$alkyl, e.g. benzyl, or
- heterocyclyl$C_{0-4})$alkyl, wherein heterocyclyl includes aromatic or aliphatic heterocyclyl of 3 to 12 ring members and 1 to 4 heteroatoms selected from N, O, S;

e.g. wherein substituents include one or more, e.g. 1 or 2, $(C_{1-4})$alkyl, wherein alkyl optionally is substituted by $(C_{6-18})$aryl, such as 1-phenylethyl, $(C_{1-4})$alkoxy, such as methoxy, halo$(C_{1-4})$alkoxy, such as trifluoromethoxy, $(C_{6-18})$aryl$(C_{1-4})$alkoxy, such as benzyloxy, halogen, hydroxy, tri$(C_{1-6})$alkylsilyloxy, such as (dimethyl)(tert-butyl)silyloxy, $(C_{1-4})$alkoxycarbonyl, such as ethoxycarbonyl, halogen or $NH_2SO_3$, with the proviso that compounds are excluded wherein $R_1$ is phenyl or 2-methylphenyl if R is hydrogen, or one or two chloro or bromo.

In a compound of formula I preferably

R is hydrogen, $NHSO_3$, halogen, or $(C_{1-4})$alkoxy, wherein the alkyl part is unsubstituted or substituted, e.g. unsubstituted or substituted by $(C_{6-12})$aryl, such as benzyloxy, $R_1$ is $(C_{6-22})$alkyl, $(C_{6-12})$cycloalkyl, such as cyclohexyl, $(C_{6-18})$aryl, such as phenyl, naphthyl, biphenylyl, phenyl anellated or fused with a crown ether, $(C_{1-4})$alkyl$(C_{6-18})$aryl, e.g. benzyl, or heterocyclyl comprising 6 to 12 ring members and 1 to 4 heteroatoms selected from N, O, S, such as piperidine, wherein cycloalkyl, aryl or heterocyclyl are unsubstituted or substituted, e.g. unsubstituted or substituted by one or more, e.g. 1 or 2, $(C_{1-4})$alkyl, wherein alkyl optionally is substituted by $(C_{6-18})$aryl, such as 1-phenylethyl, $(C_{1-4})$alkoxy, such as methoxy, halo$(C_{1-4})$alkoxy, such as trifluoromethoxy, $(C_{6-18})$aryl$(C_{1-4})$alkoxy, such as benzyloxy, halogen, hydroxy, tri$(C_{1-6})$alkylsilyloxy, such as (dimethyl)(tert-butyl)silyloxy, $(C_{1-4})$alkoxycarbonyl, such as ethoxycarbonyl or $NH_2SO_3$, with the proviso that compounds are excluded wherein $R_1$ is phenyl or 2-methylphenyl when R is hydrogen or one or two chloro.

In a compound of formula I R is preferably in position 7 of the 3,4-dihydro-benzo[e][1,3]oxazin-2-one ring.

In another aspect the present invention provides a compound of formula I, which is a compound of formula

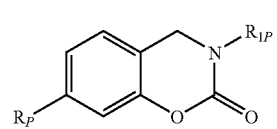

IP wherein $R_P$ is as defined for R, and $R_{1P}$ is as defined for $R_1$ above, with the proviso that compounds are excluded wherein $R_{1P}$ is phenyl or 2-methylphenyl when $R_P$ is hydrogen, chloro or bromo.

In a compound of formula I or of formula $I_P$ each single defined substituent may be a preferred substituent, e.g. independently of each other substituent defined.

In another aspect the present invention provides a compound of formula I, selected from the group consisting of
3-Cyclohexyl-7-hydroxy-3,4-dihydro-benzo[e][1,3]oxazin-2-one,
7-Hydroxy-3-(4-methoxy-phenyl)-3,4-dihydro-benzo[e][1,3]oxazin-2-one,
7-Hydroxy-3-(4-hydroxy-cyclohexyl)-3,4-dihydro-benzo[e][1,3]oxazin-2-one,
7-Hydroxy-3-phenyl-3,4-dihydro-benzo[e][1,3]oxazin-2-one,
7-Hydroxy-3-(3-hydroxy-phenyl)-3,4-dihydro-benzo[e][1,3]oxazin-2-one,
7-Hydroxy-3-(4-hydroxy-phenyl)-3,4-dihydro-benzo[e][1,3]oxazin-2-one,
Sulfamic acid 4-(7-hydroxy-2-oxo-4H-benzo[e][1,3]oxazin-3-yl)-phenyl ester,
3-[4-(tert-Butyl-dimethyl-silanyloxy)-phenyl]-7-hydroxy-3,4-dihydro-benzo[e][1,3]oxazin-2-one,
3-(6,7,9,10,12,13,15,16,18,19-Decahydro-5,8,11,14,17,20-hexaoxa-benzocyclooxydecene-2-yl)-7-hydroxy-3,4-dihydro-benzo[e][1,3]oxazin-2-one,
3-Benzyl-7-hydroxy-3,4-dihydro-benzo[e][1,3]oxazin-2-one,
7-Hydroxy-3-(4-trifluoromethoxy-phenyl)-3,4-dihydro-benzo[e][1,3]oxazin-2-one,
Sulfamic acid 2-oxo-3-(3-sulfamoyloxy-phenyl)-3,4-dihydro-2H-benzo[e][1,3]oxazin-7-yl ester, 3-(4-Methoxy-phenyl)-3,4-dihydro-benzo[e][1,3]oxazin-2-one, Sulfamic acid 3-cyclohexyl-2-oxo-3,4-dihydro-2H-benzo[e][1,3]oxazin-7-yl ester, Sulfamic acid 2-oxo-3-(4-sulfamoyloxy-phenyl)-3,4-dihydro-2H-benzo[e][1,3]oxazin-7-yl ester, 3-Biphenyl-4-yl-3,4-dihydro-benzo[e][1,3]oxazin-2-one, Sulfamic acid 3-(4-methoxy-phenyl)-2-oxo-3,4-dihydro-2H-benzo[e][1,3]oxazin-7-yl ester, Sulfamic acid 2-oxo-3-phenyl-3,4-dihydro-2H-benzo[e][1,3]oxazin-7-yl ester, 3-Hexyl-7-hydroxy-3,4-dihydro-benzo[e][1,3]oxazin-2-one, Sulfamic acid 3-(4-hydroxy-phenyl)-2-oxo-3,4-dihydro-2H-benzo[e][1,3]oxazin-7-yl ester, 7-Hydroxy-3-naphthalen-1-yl-3,4-dihydro-benzo[e][1,3]oxazin-2-one, 3-(4-Bromo-phenyl)-3,4-dihydro-benzo[e][1,3]oxazin-2-one, Sulfamic acid 3-benzyl-2-oxo-3,4-dihydro-2H-benzo[e][1,3]oxazin-7-yl ester, 4-(7-Benzyloxy-2-oxo-4H-benzo[e][1,3]oxazin-3-yl)-benzoic acid methyl ester, Sulfamic acid 4-(7-methoxy-2-oxo-4H-benzo[e][1,3]oxazin-3-yl)-phenyl ester, 3-(4-Hydroxy-phenyl)-7-methoxy-3,4-dihydro-benzo[e][1,3]oxazin-2-one, 7-Fluoro-3-(4-methoxy-phenyl)-3,4-dihydro-benzo[e][1,3]oxazin-2-one, 7-Fluoro-3-(3-methoxy-phenyl)-3,4-dihydro-benzo[e][1,3]oxazin-2-one, 3-(3-Benzyloxy-phenyl)-3,4-dihydro-benzo[e][1,3]oxazin-2-one, and 4-(2-Oxo-4H-benzo[e][1,3]oxazin-3-yl)-1-(1-phenyl-ethyl)-piperidine-2-carboxylic acid ethyl ester, e.g. including (S)-4-(2-Oxo-4H-benzo[e][1,3]oxazin-3-yl)-1-((R)-1-phenyl-ethyl)-piperidine-2-carboxylic acid ethyl ester, In another aspect the present invention provides a compound of formula

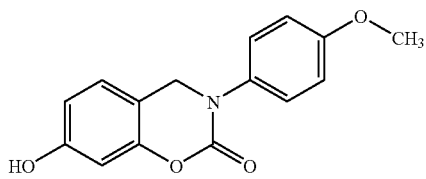

or of formula

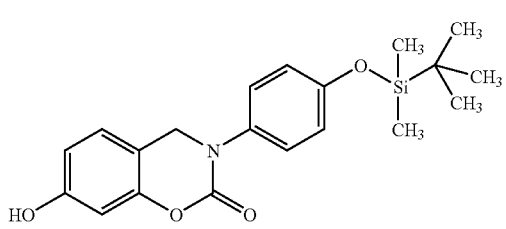

or a compound of formula

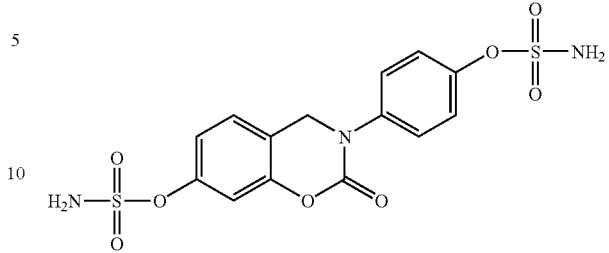

In another aspect the present invention provides a compound selected from the group consisting of 7-Hydroxy-3,4-dihydro-benzo[e][1,3]oxazin-2-ones, such as 3-($C_{6-12}$)Alkyl-7-hydroxy-3,4-dihydro-benzo[e][1,3]oxazin-2-ones, e.g.

3-Hexyl-7-hydroxy-3,4-dihydro-benzo[e][1,3]oxazin-2-ones, 3-($C_{6-12}$)Aryl($C_{1-4}$)alkyl-7-hydroxy-3,4-dihydro-benzo[e][1,3]oxazin-2-ones, e.g.

3-Benzyl-7-hydroxy-3,4-dihydro-benzo[e][1,3]oxazin-2-ones, 3-($C_{6-12}$)cycloalkyl-7-hydroxy-3,4-dihydro-benzo[e][1,3]oxazin-2-ones, e.g.

3-(cyclohexyl-7-hydroxy-3,4-dihydro-benzo[e][1,3]oxazin-2-ones, 3-(hydroxy-cyclohexyl-7-hydroxy-3,4-dihydro-benzo[e][1,3]oxazin-2-ones, 3-($C_{6-18}$)Aryl-7-hydroxy-3,4-dihydro-benzo[e][1,3]oxazin-2-ones, e.g.

3-Naphthalenyl-7-Hydroxy-3,4-dihydro-benzo[e][1,3]oxazin-2-ones,

3-Phenyl-7-Hydroxy-3,4-dihydro-benzo[e][1,3]oxazin-2-ones, such as 3-(Trifluoromethoxy-phenyl)-7-hydroxy-3,4-dihydro-benzo[e][1,3]oxazin-2-ones, 3-[Tri($C_{1-6}$)alkyl-silanyloxy)-phenyl]-7-hydroxy-3,4-dihydro-benzo[e][1,3]oxazin-2-ones, 3-(Aminosulfonoyl-phenyl)-7-hydroxy-3,4-dihydro-benzo[e][1,3]oxazin-2-ones, 3-(Methoxy-phenyl)-7-hydroxy-3,4-dihydro-benzo[e][1,3]oxazin-2-ones, 3-(Hydroxy-phenyl)-7-hydroxy-3,4-dihydro-benzo[e][1,3]oxazin-2-ones, 3-(Crown ether-fused phenyl)-7-hydroxy-3,4-dihydro-benzo[e][1,3]oxazin-2-ones, 7-($C_{1-6}$)Alkoxy-3,4-dihydro-benzo[e][1,3]oxazin-2-ones, such as 7-Methoxy-3,4-dihydro-benzo[e][1,3]oxazin-2-ones, e.g.

3-(Hydroxy-phenyl)-7-methoxy-3,4-dihydro-benzo[e][1,3]oxazin-2-ones, 3-(Aminosulfonoyl-phenyl)-7-methoxy-3,4-dihydro-benzo[e][1,3]oxazin-2-ones, 7-Halo-3,4-dihydro-benzo[e][1,3]oxazin-2-ones, such as 3-($C_{6-18}$)aryl-7-halo-3,4-dihydro-benzo[e][1,3]oxazin-2-ones, e.g.

3-Phenyl-7-halo-3,4-dihydro-benzo[e][1,3]oxazin-2-ones,

3-[($C_{6-18}$)aryl($C_{1-4}$)alkoxy]-3,4-dihydro-benzo[e][1,3]oxazin-2-ones, such as 3-(Benzyloxy-phenyl)-3,4-dihydro-benzo[e][1,3]oxazin-2-ones, 3-[($C_{12-18}$)Aryl]-3,4-dihydro-benzo[e][1,3]oxazin-2-ones, such as 3-Biphenylyl-3,4-dihydro-benzo[e][1,3]oxazin-2-ones,
3-[($C_{1-4}$)Alkoxy-phenyl)]-3,4-dihydro-benzo[e][1,3]oxazin-2-ones, such as
3-(Methoxy-phenyl)-3,4-dihydro-benzo[e][1,3]oxazin-2-ones,
3-Heterocyclyl-3,4-dihydro-benzo[e][1,3]oxazin-2-ones,
  e.g. wherein heterocyclyl has 6 to 18 ring members, such as 6, e.g. including aliphatic and aromatic heterocyclyl, such as aliphatic heterocyclyl, e.g. including fused heterocyclyl ring systems, e.g. heterocyclyl anellated with another aliphatic, aromatic or heterocyclic ring (system) and single heterocyclyl rings, such as single heterocyclic rings, e.g. having 1 to 6 heteroatoms selected from N, O, S, e.g. one, e.g. N; such as
3-Piperidinyl-3,4-dihydro-benzo[e][1,3]oxazin-2-ones, and
Sulfamic acid 2-oxo-3,4-dihydro-2H-benzo[e][1,3]oxazin-7-yl esters, such as
Sulfamic acid 3-[($C_{6-18}$)aryl($C_{1-4}$)alkyl]-2-oxo-3,4-dihydro-2H-benzo[e][1,3]oxazin-7-yl esters, e.g.
Sulfamic acid 3-benzyl-2-oxo-3,4-dihydro-2H-benzo[e][1,3]oxazin-7-yl esters,
Sulfamic acid 3-($C_{6-12}$)cycloalkyl-2-oxo-3,4-dihydro-2H-benzo[e][1,3]oxazin-7-yl esters, e.g.
Sulfamic acid 3-cyclohexyl-2-oxo-3,4-dihydro-2H-benzo[e][1,3]oxazin-7-yl esters,
Sulfamic acid 3-[($C_{6-18}$)aryl]-2-oxo-3,4-dihydro-2H-benzo[e][1,3]oxazin-7-yl esters, e.g.
Sulfamic acid 2-oxo-3-phenyl-3,4-dihydro-2H-benzo[e][1,3]oxazin-7-yl esters
Sulfamic acid 3-(hydroxy-phenyl)-2-oxo-3,4-dihydro-2H-benzo[e][1,3]oxazin-7-yl esters,
Sulfamic acid 3-[4-($C_{1-4}$)alkoxy-phenyl]-2-oxo-3,4-dihydro-2H-benzo[e][1,3]oxazin-7-yl esters, such as
Sulfamic acid 3-(methoxy-phenyl)-2-oxo-3,4-dihydro-2H-benzo[e][1,3]oxazin-7-yl esters,
Sulfamic acid 2-oxo-3-(sulfamoyloxy-phenyl)-3,4-dihydro-2H-benzo[e][1,3]oxazin-7-yl esters.

Any group defined herein may comprise 1 to 24 carbon atoms.

Any group defined herein may be unsubstituted or substituted, e.g. one or morefold. Substituents include such as mentioned above in the meaning of R, $R_1$, $R_P$ and $R_{1P}$.

Compounds provided by the present invention are hereinafter designated as "compound(s) of (according to) the present invention". A compound of formula I includes a compound of formula $I_P$. A compound of the present invention includes a compound in any form, e.g. in free form, in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention may exist in the form of isomers and mixtures thereof; e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates. A compound of the present invention may be present in the (R)-, (S)- or (R,S)-configuration preferably in the (R)- or (S)-configuration regarding specified positions in the compound.

For example, a compound provided by the present invention may be in the (R)- and in the (S)-configuration, e.g. including mixtures thereof, regarding a substituent attached to a cycloalkyl or piperidinyl group, and is preferably in the (R)- or in the (S-)configuration. Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of the present invention, where tautomers can exist.

In another aspect the present invention provides a process for the production of a compound of formula I, comprising the steps of reacting a compound of formula

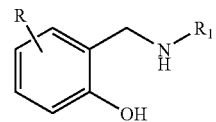

III wherein R and $R_1$ are as defined above, with carbonyldiimidazole in the presence of a base, e.g. triethylamine, and isolating a compound of formula I obtained from the reaction mixture.

A compound of formula III may be e.g. obtained by reacting a compound of formula

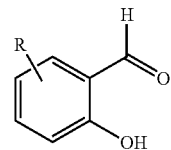

II wherein R is as defined above with a compound of formula

and isolating a compound of formula III obtained from the reaction mixture.

In an intermediate of formula II or of formula III (starting materials), functional groups, if present, optionally may be in protected form or in the form of a salt, if a salt-forming group is present. Protecting groups, optionally present, may be removed at an appropriate stage, e.g. according, e.g. analogously, to a method as conventional A compound of formula I thus obtained may be converted into another compound of formula I, e.g. or a compound of formula I obtained in free form may be converted into a salt of a compound of formula I and vice versa.

A compound of formula I$_P$ may be e.g. obtained by a process comprising the steps a. reacting a compound of formula

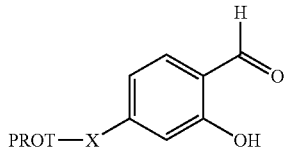

II$_P$ or a compound of formula

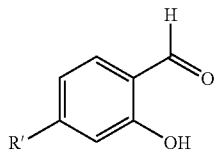

II'$_P$ wherein PROT is either a protecting group such as benzyl, or PROT is (C$_{1-4}$)alkyl, halo(C$_{1-4}$)alkyl, or (C$_{6-18}$)aryl (C$_{1-4}$)alkyl, X is S or O and R' is hydrogen or halo.

with a compound of formula

H$_2$N—R$_{1P}$ wherein R$_{1P}$ is as defined above, in the presence of a reducing agent, such as NaBH$_4$, to obtain a compound of formula

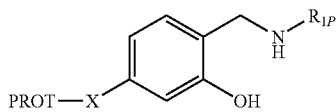

III$_P$ or of formula

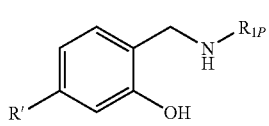

III'$_P$ wherein PROT, X and R$_{1P}$ are as defined above, b. reacting a compound of formula III$_P$, or III'$_P$ obtained in step a. with carbonyldiimidazole in the presence of a base, e.g. triethylamine, to obtain a compound of formula

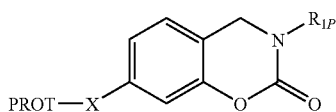

IV$_P$ or of formula

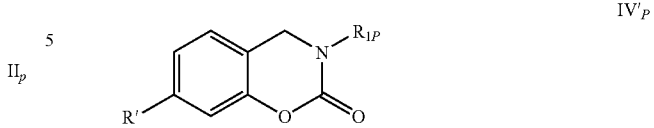

IV'$_P$ c. optionally, if R$_{1P}$ comprises a substituent which is hydroxy, reacting said hydroxy group to obtain a substituted hydroxy group with a reactive derivative of said substituent, e.g. in case of a substituent which is tri(C$_{1-6}$)alkylsilyloxy with a tri(C$_{1-6}$)alkylsilylhalogenide, such as a chloride, e.g. in the presence of imidazole, d. optionally deprotecting, e.g. removing PROT in a compound obtained in step b. or step c., e.g. by catalytic hydrogenation, to obtain a compound of formula I$_P$ wherein R$_P$ is hydroxy or mercapto, e. optionally sulfonylating the hydroxy group in position 7 in a compound of formula IV$_P$ obtained in step d. and further reacting with NH$_3$, to obtain a compound of formula I wherein R$_P$ is NH$_2$SO$_3$, and f. isolating a compound of formula I$_P$ from the reaction mixture.

7-Hydroxy-3,4-dihydro-benzo[e][1,3]oxazin-2-ones, 7-(C$_{1-6}$)alkoxy-3,4-dihydro-benzo[e][1,3]oxazin-2-ones, 7-halo-3,4-dihydro-benzo[e][1,3]oxazin-2-ones, 3-[(C$_{6-18}$)aryl(C$_{1-4}$)alkoxy]-3,4-dihydro-benzo[e][1,3]oxazin-2-ones, 3-[(C$_{6-18}$)aryl]-3,4-dihydro-benzo[e][1,3]oxazin-2-ones, 3-[(C$_{1-4}$)alkoxy-phenyl)]-3,4-dihydro-benzo[e][1,3]oxazin-2-ones, 3-heterocyclyl-3,4-dihydro-benzo[e][1,3]oxazin-2-ones, or sulfamic acid 2-oxo-3,4-dihydro-2H-benzo[e][1,3]oxazin-7-yl esters provided by the present invention may be obtained analogously to a process as set out for the production of a compound of formula I or I$_P$.

Intermediates (starting materials) of formula II, II$_P$, II$_P$', III, III$_P$, III$_P$', IV$_P$ or IV$_P$' are known or may be prepared according, e.g. analogously, to a method as conventional or as specified herein.

Any compound described herein, e.g. a compound of the present invention and intermediates of formula II, II$_P$, II$_P$', III, III$_P$, III$_P$', IV$_P$ or IV$_P$' may be prepared as appropriate, e.g. according, e.g. analogously, to a method as conventional, e.g. or as specified herein.

The compounds of the present invention, e.g. including a compound of formula I, exhibit pharmacological activity and are therefore useful as pharmaceuticals. E.g., the compounds of the present invention are found to inhibit MIF activity, e.g. MIF enzyme activity.

The natural substrates of MIF enzyme activity are not yet known with certainty. However, the tautomerase activity of MIF can be readily demonstrated with the substrates D-dopachrome and p-hydroxyphenylpyruvate (HPP) (see e.g. Rosengren et al. Molec. Med. 2:143-149, 1996; Rosengren E, FEBS Lett. 417:85-88, 1997).

HPP-ASSAY

The assay used herein is such HPP assay adopted to the microtiter plate format:

Human MIF protein is purified according to Bernhagen et al. Biochemistry, 33:14144-14155, 1994. Dilutions of the enzyme are prepared in 50 mM sodium phosphate buffer, 1 mM EDTA, pH 6.5.

HPP is obtained from Aldrich. A stock solution of 60 mM HPP in ethanol is prepared and kept for maximally 4 hours on ice. The working solution (600 μM) of the substrate is prepared by diluting an aliquot of the stock solution with 50 mM sodium phosphate buffer, 1 mM EDTA, pH 6.5.

UV-transparent microtiter plates (96-well) are obtained from Corning (Cat# 3635). Inhibitor and enzyme solutions are pipetted manually using an Eppendorf 12-channel pipette. Addition of substrate to start the reaction is performed with an Igel 96 pipetting station (OpalJena, Jena, Germany), which allows simultaneous addition of fluid to all 96 wells of the plates.

Optical density (OD) is determined using a SPECTRAmax 250 reader (Molecular Devices). The reader is operated with the SoftmaxPro 2.6.1 software.

Assay: Three wells of the microtiter plates are filled with buffer only, to allow for blanking. Into the test wells are pipetted consecutively:

50 µl inhibitor dilution (or buffer for control),
50 µl enzyme dilution (55 nM; final concentration in assay: 18.3 nM),
50 µl freshly diluted substrate working solution (600 µM; final concentration: 200 µM).

The last step is performed using the 96-channel pipetting device. The plate is then immediately (i.e. within a few seconds) transferred manually to the SPECTRAmax 250 reader and the optical density is determined (310 nm).

From the data obtained, $IC_{50}$ values are calculated using Excel™ and XLfit™ software.

The compounds of the present invention show activity in that HPP Assay, i.e. the compounds of the present invention inhibit MIF-tautomerase activity in a nanomolar range up to the low micromolar range and are therefore indicated for the treatment of disorders (diseases) mediated by MIF activity:

Disorders, e.g. including diseases, mediated by MIF activity and which are prone to be successfully treated with MIF antagonists, e.g. with compounds of the present invention, include disorders, wherein the activity of MIF play a causal or contributory role.

Such disorders (diseases) include but are not limited to
disorders associated with inflammation
e.g. including (chronic) inflammatory disorders, disorders related with the inflammation of the bronchi, e.g. including bronchitis, cervix, e.g. including cervicitis, conjunctiva, e.g. conjunctivitis, esophagus, e.g. esophagitis, heart muscle, e.g. myocarditis, rectum, e.g. proctitis, sclera, e.g. scleritis, gums, involving bone, pulmonary inflammation (alveolitis), airways, e.g. asthma, such as bronchial asthma, acute respiratory distress syndrome (ARDS), inflammatory skin disorders such as contact hypersensitivity, atopic dermatitis; fibrotic disease (e.g., pulmonary fibrosis), encephalitis, inflammatory osteolysis,
disorders associated with conditions of the immune system,
immune, such as autoimmune disorders e.g. including Graves' disease, Hashimoto's disease (chronic thyroiditis), multiple sclerosis, rheumatoid arthritis, arthritis, gout, osteoarthritis, scleroderma, lupus syndromes, systemic lupus erytomatosis, Sjgren's syndrome, psoriasis, inflammatory bowel disease, including Crohn's disease, colitis, e.g. ulcerative colitis; sepsis, septic shock, autoimmune hemolytic anemia (AHA), autoantibody triggered urticaria, pemphigus, nephritis, glomerulonephritis, Goodpastur syndrome, ankylosing spondylitis, Reiter's syndrome, polymyositis, dermatomyositis,
disorders associated with cytokine-mediated toxicity,
e.g. including interleukin-2 toxicity,
disorders associated with the bone,
e.g. including osteoporosis, osteoarthritis,
disorders associated with the brain and the nerves,
neurodegenerative disorders, e.g. including disorders of the central nervous system as well as disorders of the peripheral nervous system, e.g. CNS disorders including central nervous system infections, brain injuries, cerebrovascular disorders and their consequences, Parkinson's disease, corticobasal degeneration, motor neuron disease, dementia including ALS, multiple sclerosis, traumatic disorders, including trauma and inflammatory consequences of trauma, traumatic brain injury, stroke, post-stroke, post-traumatic brain injury,
small-vessel cerebrovascular disease, eating disorders; further dementias, e.g. including Alzheimer's disease, vascular dementia, dementia with Lewy-bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld Jakob dementia, HIV dementia, schizophrenia with dementia, Korsakoff's psychosis,
cognitive-related disorders, such as mild cognitive impairment, age associated memory impairment, age-related cognitive decline, vascular cognitive impairment, attention deficit disorders, attention deficit hyperactivity disorders, and memory disturbances in children with learning disabilities; conditions associated with the hypothalamic-pituitary-adrenal axis,
neuronal disorders, e,g. including neuronal migration disorders, hypotonia (reduced muscle tone), muscle weakness, seizures, developmental delay (physical or mental development difficulty), mental retardation, growth failure, feeding difficulties, lymphedema, microcephaly, symptoms affecting the head and the brain, motor dysfunction;
disorders associated with the eye,
e.g. including uveoritinitis, vitreoretinopathy, corneal disease, iritis, iridocyclitis, cataracts, uveitis, diabetic retinopathy, retinitis pigmentosa, conjunctivitis,
disorders associated with the gastrointestinal tract
e.g. including colitis, inflammatory bowel disease, colitis, Crohn's disease, ulcerative colitis, peptic ulceration, gastritis, oseophagitis,
disorders associated with the heart and vascular conditions
e.g. including cardiovascular disorders, e.g. including cardiac failure, cardiac infarction, cardiac hypertrophy, heart failure, e.g. including all forms of heart pumping failures such as high-output and low-output, acute and chronic, right sided or left-sided, systolic or diastolic, independent of the underlying cause; myocardial infarction (MI), MI prophylaxis (primary and secondary prevention), acute treatment of MI, prevention of complications; heart disorders, proliferative vascular disorders, vasculitides, polyarteritis nodosa, inflammatory consequences of ischemia, ischemic heart disease, myocardial infarction, stroke, peripheral vascular disease, pulmonary hypertension,
ischemic disorders, e.g. including myocardial ischemia, e.g. stable angina, unstable angina, angina pectoris, bronchitis; asymptomatic arrhythmias such as all forms of atrial and ventricular tachyarrhythmias, atrial tachycardia, atrial flutter, atrial fibrillation, atrio-ventricular reentrant tachycardia, preexitation syndrome, ventricular tachycardia, ventricular flutter, ventricular fibrillation, bradycardic forms of arrhythmias; arrhythmia, chronic obstructive pulmonary disease, hypertension, such as systolic or diastolic high blood pressure, e.g essential and secondary hypertension, e.g. including hypertensive vascular disorders, such as primary as well as all kinds of secondary arterial hypertension, renal, endocrine, neurogenic and others;

peripheral vascular disorders in which arterial and/or venous flow is reduced resulting in an imbalance between blood supply and tissue oxygen demand, e.g. including artherosclerosis, chronic peripheral arterial occlusive disease (PAOD), acute arterial thrombosis and embolism, inflammatory vascular disorders, Raynaud's phenomenon and venous disorders; atherosclerosis, a disease in which the vessel wall is remodeled, e.g. including accumulation of cells, both smooth muscle cells and monocyte/macrophage inflammatory cells, in the intima of the vessel wall;

hypotension, disorders associated with the liver and the kidneys, e.g. including renal disorders, kidney disorders, e.g. acute kidney failure, acute renal disease, liver disorders, e.g. cirrhosis, hepatitis, liver failure, cholestasis, hepatitis, sclerosing cholangitis, primary billiary cirrhosis, disorders associated with stomach or pancreas conditions stomach disorders, e.g. gastric ulcer, gastrointestinal ulcer, pancreatic disorders pancreatic fatigue, disorders associated with the respiratory tract and lung e.g. including pulmonary disorders, chronic pulmonary disease, acute (adult) respiratory distress syndrome (ARDS), asthma, asthma bronchitis, bronchiectasis, diffuse interstitial lung disorders, pneumonioses, fibrosing aveolitis, lung fibrosis, disorders associated with skin and connective tissue conditions e.g. including eczema, atopic dermatitis, contact dermatitis, psoriasis, dermatomyositis, Sjörgen's syndrome, Churg-Struass syndrome, sunburn, skin cancer, wound healing, disorders associated with allergic conditions, e.g. including delayed-type hypersensitivity, allergic conjunctivitis, drug allergies, rhinitis, allergic rhinitis, vasculitis, contact dermatitis;

disorders associated with angiogenesis, e.g. including insufficient ability to recruit blood supply, disorders characterised by modified angiogenesis, tumor associated angiogenesis, disorders associated with cancer and cell overproliferation, e.g. including premalignant conditions, hyperproliferative disorders, cancers whether primary or metastatic, cervical and metastatic cancer, cancer originating from uncontrolled cellular proliferation, solid tumors, such as such as described in WO02066019, including nonsmall cell lung cancer, cervical cancer; tumor growth, lymphoma, B-cell or T-cell lymphoma, benign tumors, benign dysproliferative disorders, renal carcinoma, esophageal cancer, stomach cancer, renal carcinoma, bladder cancer, breast cancer, colon cancer, lung cancer, melanoma, nasopharyngeal cancer, osteocarcinoma, ovarian cancer, uterine cancer; prostate cancer, skin cancer, leukemia, tumor neovascularization, angiomas, myelodysplastic disorders, unresponsiveness to normal death-inducing signals (immortalization), increased cellular motility and invasiveness, genetic instability, dysregulated gene expression, (neuro)endocrine cancer (carcinoids), blood cancer, lymphocytic leukemias, neuroblastoma; soft tissue cancer, prevention of metastasis, disorders associated with diabetic conditions, e.g. including diabetes (type I diabetes, type II diabetes), diabetic retinopathy, insulin-dependent diabetes, diabetes mellitus, gestational diabetes), insulin hyposecretion, obesity;

disorders associated with endiometriosis, testicular dysfunctions, disorders associated with infectious disorders, e.g. with chronic infectious conditions, e.g. including bacterial disorders, otitis media, Lyme disease, thryoditis, viral disorders, parasitic disorders, fungal disorders, malaria, e.g. malaria anemia, sepsis, severe sepsis, septic shock, e.g. endotoxin-induced septic shock, exotoxin-induced toxic shock, infective (true septic) shock, septic shock caused by Gram-negative bacteria, pelvic inflammatory disease, AIDS, enteritis, pneumonia; meningitis, encephalitis, disorders associated with myasthenia gravis, disorders associated with nephritis, e.g. including glomerulonephritis, interstitial nephritis, Wegener's granulomatosis, disorders associated with pain, e.g. associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation);

non-central neuropathic pain, e.g. including that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia;

pain associated with peripheral nerve damage, central pain (i.e. due to cerebral ischemia) and various chronic pain i.e., lumbago, back pain (low back pain), inflammatory and/or rheumatic pain;

headache pain (for example, migraine with aura, migraine without aura, and other migraine disorders), episodic and chronic tension-type headache, tension-type like headache, cluster headache, and chronic paroxysmal hemicrania;

visceral pain such as pancreatis, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome 15 and protatodynia;

acute pain, for example postoperative pain, and pain after trauma;

disorders associated with rheumatic disorders, e.g. including arthritis, rheumatoid arthritis, osteoarthritis, psoriatic arthritis, crystal arthropathies, gout, pseudogout, calcium pyrophosphate deposition disease, lupus syndromes, systemic lupus erythematosus, sclerosis, scleroderma, multiple sclerosis, artherosclerosis, arteriosclerosis, spondyloarthropathies, systemic sclerosis, reactive arthritis, Reiter's syndrome, ankylosing spondylitis, polymyositis, disorders associated with sarcoidosis, disorders associated with transplantation, e.g. including transplant rejection crisis and other disorders following transplantation, such as organ or tissue transplant rejection, e.g. for the treatment of recipients of e.g. heart, lung, combined heart-lung, liver, kidney, pancreatic, skin, corneal transplants, graft versus host disease, such as following bone marrow transplantation, ischemic reperfusion injury.

More preferably the compounds of the present invention may be useful for the treatment of disorders (diseases) associated with inflammation, the immune system, cancers, allergic conditions, transplantation, infections, such as rheumatoid arthritis, inflammatory bowel disease, e.g. colitis (including Crohn's disease and ulcerative colitis), atopic dermatitis, psoriasis, proliferative vascular disorders, acute respiratory distress syndrome (ARDS), asthma, multiple sclerosis, graft versus host disease, lupus syndromes, tumor growth and angiogenesis, malaria.

For pharmaceutical use a compound of the present invention includes a compound of formula I, wherein $R_1$ is phenyl or 2-methylphenyl if R is hydrogen or one or two chloro or bromo, optionally in the form of a pharmaceutically acceptable salt, and includes a compound of formula $I_P$, wherein $R_{1P}$ is phenyl or 2-methylphenyl if $R_P$ is hydrogen, chloro or bromo, optionally in the form of a pharmaceutically acceptable salt.

In another aspect the present invention provides
A compound of the present invention for use as a pharmaceutical, e.g. for the treatment of disorders mediated by MIF activity;
The use of a compound of the present invention as a pharmaceutical, e.g. for the treatment of disorders mediated by MIF activity;

e.g. wherein a compound of the present invention includes
a compound of the present invention,
a compound of formula I, wherein $R_1$ is phenyl or 2-methylphenyl if R is hydrogen or one or two chloro or bromo, optionally in the form of a pharmaceutically acceptable salt, or
a compound of formula $I_P$, wherein $R_{1P}$ is phenyl or 2-methylphenyl if $R_P$ is hydrogen, chloro or bromo, optionally in the form of a pharmaceutically acceptable salt.

For pharmaceutical use one or more compounds of the present invention may be used, e.g. one, or a combination of two or more compounds of the present invention, preferably one compound of the present invention is used.

A compound of the present invention may be used as a pharmaceutical in the form of a pharmaceutical composition.

In another aspect the present invention provides a pharmaceutical composition comprising a compound of the present invention in association with at least one pharmaceutically acceptable excipient, e.g. appropriate carrier and/or diluent, e.g. including fillers, binders, disintegrators, flow conditioners, lubricants, sugars or sweeteners, fragrances, preservatives, stabilizers, wetting agents and/or emulsifiers, solubilizers, salts for regulating osmotic pressure and/or buffers, e.g. wherein a compound of the present invention includes
a compound of the present invention,
a compound of formula I, wherein $R_1$ is phenyl or 2-methylphenyl if R is hydrogen or one or two chloro or bromo, optionally in the form of a pharmaceutically acceptable salt, or
a compound of formula $I_P$, wherein $R_{1P}$ is phenyl or 2-methylphenyl if $R_P$ is hydrogen, chloro or bromo, optionally in the form of a pharmaceutically acceptable salt.

In another aspect the present invention provides
a pharmaceutical composition of the present invention for use of treating disorders which are mediated by MIF activity.
the use of a pharmaceutical composition of the present invention for treating disorders which are mediated by MIF activity, e.g. wherein a compound of the present invention includes
a compound of the present invention,
a compound of formula I, wherein $R_1$ is phenyl or 2-methylphenyl if R is hydrogen or one or two chloro or bromo, optionally in the form of a pharmaceutically acceptable salt, or
a compound of formula $I_P$, wherein $R_{1P}$ is phenyl or 2-methylphenyl if $R_P$ is hydrogen, chloro or bromo, optionally in the form of a pharmaceutically acceptable salt.

In a further aspect the present invention provides a method of treating disorders which are mediated by MIF activity, e.g. including disorders as specified above, which treatment comprises administering to a subject in need of such treatment an effective amount of a compound of the present invention; e.g. in the form of a pharmaceutical composition;

e.g. wherein a compound of the present invention includes
a compound of the present invention,
a compound of formula I, wherein $R_1$ is phenyl or 2-methylphenyl if R is hydrogen or one or two chloro or bromo, optionally in the form of a pharmaceutically acceptable salt, or
a compound of formula $I_P$, wherein $R_{1P}$ is phenyl or 2-methylphenyl if $R_P$ is hydrogen, chloro or bromo, optionally in the form of a pharmaceutically acceptable salt.

In another aspect the present invention provides
A compound of the present invention for the manufacture of a medicament, e.g. a pharmaceutical composition, for the treatment of disorders, which are mediated by MIF activity,
The use of a compound of the present invention for the manufacture of a medicament, e.g. a pharmaceutical composition, for the treatment of disorders, which are mediated by MIF activity, e.g. wherein a compound of the present invention includes
a compound of the present invention,
a compound of formula I, wherein $R_1$ is phenyl or 2-methylphenyl if R is hydrogen or one or two chloro or bromo, optionally in the form of a pharmaceutically acceptable form, or
a compound of formula $I_P$, wherein $R_{1P}$ is phenyl or 2-methylphenyl if $R_P$ is hydrogen, chloro or bromo, optionally in the form of a pharmaceutically acceptable form.

Treatment includes treatment and prophylaxis (prevention).

For such treatment, the appropriate dosage will, of course, vary depending upon, for example, the chemical nature and the pharmacokinetic data of a compound of the present invention used, the individual host, the mode of administration and the nature and severity of the conditions being treated. However, in general, for satisfactory results in larger mammals, for example humans, an indicated daily dosage includes a range from about 0.001 g to about 1.5 g, such as 0.001 g to 1.5 g, from about 0.01 mg/kg body weight to about 20 mg/kg body weight, such as 0.01 mg/kg body weight to 20 mg/kg body weight, for example administered in divided doses up to four times a day.

A compound of the present invention may be administered to larger mammals, for example humans, by similar modes of administration at similar dosages than conventionally used with other mediators, e.g. low molecular weight inhibitors, of MIF activity.

A compound of the present invention may be administered by any conventional route, for example enterally, e.g. including nasal, buccal, rectal, oral, administration; parenterally, e.g. including intravenous, intramuscular, subcutaneous administration; or topically; e.g. including epicutaneous, intranasal, intratracheal administration; via medical devices for local delivery, e.g. stents, e.g. in form of coated or uncoated tablets, capsules, (injectable) solutions, solid solutions, suspensions, dispersions, solid dispersions; e.g. in the form of ampoules, vials, in the form of creams, gels, pastes, inhaler powder, foams, tinctures, lip sticks, drops, sprays, or in the form of suppositories.

The compounds of the present invention may be administered in the form of a pharmaceutically acceptable salt, or in free form; optionally in the form of a solvate. A compound of the present invention in the form of a salt and/or in the form of a solvate exhibit the same order of activity as a compound of the present invention in free form.

A compound of the present invention may be used for any method or use as described herein alone or in combination with one or more, at least one, other, second drug substance.

In another aspect the present invention provides
A combination of a compound of the present invention with at least one second drug substance;
A pharmaceutical combination comprising a compound of the present invention in combination with at least one second drug substance;
A pharmaceutical composition comprising a compound of the present invention in combination with at least one second drug substance and one or more pharmaceutically acceptable excipient(s);
A compound of the present invention in combination with at least one second drug substance, e.g. in the form of a pharmaceutical combination or composition, for use in any method as defined herein, e.g.
  A combination, a pharmaceutical combination or a pharmaceutical composition, comprising a compound of the present invention and at least one second drug substance for use as a pharmaceutical;
  The use as a pharmaceutical of a compound of the present invention in combination with at least one second drug substance, e.g. in the form of a pharmaceutical combination or composition;
A method for treating disorders mediated by MIF activity in a subject in need thereof, comprising co-administering, concomitantly or in sequence, a therapeutically effective amount of a compound of the present invention and at least one second drug substance, e.g. in the form of a pharmaceutical combination or composition;
A compound of the present invention in combination with at least one second drug substance, e.g. in the form of a pharmaceutical combination or composition, for use in the preparation of a medicament for use in disorders mediated by MIF activity;

e.g. wherein a compound of the present invention includes
  a compound of the present invention,
  a compound of formula I, wherein $R_1$ is phenyl or 2-methylphenyl if R is hydrogen or one or two chloro or bromo, optionally in the form of a pharmaceutically acceptable salt, or
  a compound of formula $I_P$, wherein $R_{1P}$ is phenyl or 2-methylphenyl if $R_P$ is hydrogen, chloro or bromo, optionally in the form of a pharmaceutically acceptable salt.

Combinations include fixed combinations, in which a compound of the present invention and at least one second drug substance are in the same formulation; kits, in which a compound of the present invention and at least one second drug substance in separate formulations are provided in the same package, e.g. with instruction for co-administration; and free combinations in which a compound of the present invention and at least one second drug substance are packaged separately, but instruction for concomitant or sequential administration are given.

In another aspect the present invention provides
A pharmaceutical package comprising a first drug substance which is a compound of the present invention and at least one second drug substance, beside instructions for combined administration;
A pharmaceutical package comprising a compound of the present invention beside instructions for combined administration with at least one second drug substance;
A pharmaceutical package comprising at least one second drug substance beside instructions for combined administration with a compound of the present invention;

e.g. wherein a compound of the present invention includes
  a compound of the present invention,
  a compound of formula I, wherein $R_1$ is phenyl or 2-methylphenyl if R is hydrogen or one or two chloro or bromo, optionally in the form of a pharmaceutically acceptable salt, or
  a compound of formula $I_P$, wherein $R_{1P}$ is phenyl or 2-methylphenyl if $R_P$ is hydrogen, chloro or bromo, optionally in the form of a pharmaceutically acceptable salt.

Treatment with combinations according to the present invention may provide improvements compared with single treatment.

In another aspect the present invention provides
A pharmaceutical combination comprising an amount of a compound of the present invention and an amount of a second drug substance, wherein the amounts are appropriate to produce a synergistic therapeutic effect;
A method for improving the therapeutic utility of a compound of the present invention comprising co-administering, e.g. concomitantly or in sequence, of a therapeutically effective amount of a compound of the present invention and a second drug substance.
A method for improving the therapeutic utility of a second drug substance comprising co-administering, e.g. concomitantly or in sequence, of a therapeutically effective amount of a compound of the present invention and a second drug substance e.g. wherein a compound of the present invention includes
  a compound of the present invention,
  a compound of formula I, wherein $R_1$ is phenyl or 2-methylphenyl if R is hydrogen or one or two chloro or bromo, optionally in the form of a pharmaceutically acceptable salt, or
  a compound of formula $I_P$, wherein $R_{1P}$ is phenyl or 2-methylphenyl if $R_P$ is hydrogen, chloro or bromo, optionally in the form of a pharmaceutically acceptable salt.

A combination of the present invention and a second drug substance as a combination partner may be administered by any conventional route, for example as set out above for a compound of the present invention. A second drug may be administered in dosages as appropriate, e.g. in dosage ranges which are similar to those used for single treatment, or, e.g. in case of synergy, even below conventional dosage ranges.

Pharmaceutical compositions according to the present invention may be manufactured according, e.g. analogously, to a method as conventional, e.g. by mixing, granulating, coating, dissolving or lyophilizing processes. Unit dosage forms may contain, for example, from about 0.1 mg to about 1500 mg, such as 1 mg to about 1000 mg.

Pharmaceutical compositions comprising a combination of the present invention and pharmaceutical compositions comprising a second drug as described herein, may be provided as appropriate, e.g. according, e.g. analogously, to a method as conventional, or as described herein for a pharmaceutical composition of the present invention.

By the term "second drug substance" is meant a chemotherapeutic drug, especially any chemotherapeutic agent, other than a compound of the present invention, e.g. wherein a compound of the present invention includes
  a compound of the present invention,
    a compound of formula I, wherein $R_1$ is phenyl or 2-methylphenyl if R is hydrogen or one or two chloro or bromo optionally in the form of a pharmaceutically acceptable salt, or
    a compound of formula $I_P$, wherein $R_{1P}$ is phenyl or 2-methylphenyl if $R_P$ is hydrogen, chloro or bromo, optionally in the form of a pharmaceutically acceptable salt.

For example, a second drug substance as used herein includes e.g. anti-inflammatory and/or immunomodulatory drugs, anticancer drugs, anesthetic drugs, e.g. including other (ant)agonists of MIF activity, than compounds of the present inventions, e.g. including antibodies and low molecular weight compounds.

Anti-inflammatory and/or immunomodulatory drugs which are prone to be useful in combination with a compound of the present invention include e.g.
  mediators, e.g. inhibitors of mTOR activity, including rapamycins, e.g. rapamycin of formula

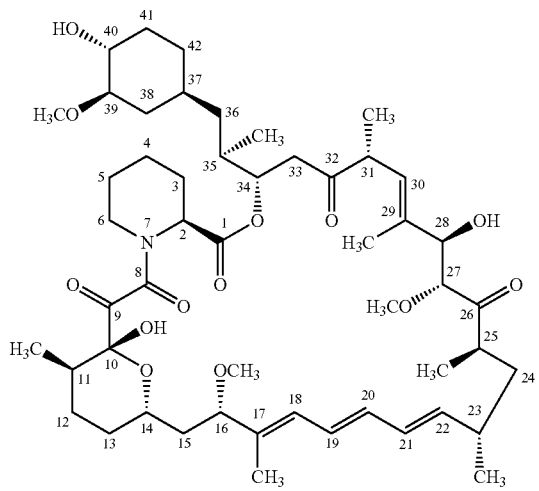

40-O-(2-hydroxyethyl)rapamycin, 32-deoxorapamycin, 16-O-substituted rapamycins such as 16-pent-2-ynyloxy-32-deoxorapamycin, 16-pent-2-ynyloxy-32 (S or R)-dihydro-rapamycin, 16-pent-2-ynyloxy-32(S or R)-dihydro-40-O-(2-hydroxyethyl)-rapamycin, 40-[3-hydroxy-2-(hydroxy-methyl)-2-methylpropanoate]-rapamycin (also known as CCI779), 40-epi-(tetrazolyl)-rapamycin (also known as ABT578), the so-called rapalogs, e.g. as disclosed in WO9802441, WO0114387 and WO0364383, such as AP23573, and compounds disclosed under the name TAFA-93 and biolimus (biolimus A9);

mediators, e.g. inhibitors, of calcineurin, e.g. cyclosporin A, FK 506;

ascomycins having immuno-suppressive properties, e.g. ABT-281, ASM981;

corticosteroids; cyclophosphamide; azathioprene; leflunomide; mizoribine;

mycophenolic acid or salt; mycophenolate mofetil;

15-deoxyspergualine or an immunosuppressive homologue, analogue or derivative thereof;

mediators, e.g. inhibitors, of bcr-abl tyrosine kinase activity;

mediators, e.g. inhibitors, of c-kit receptor tyrosine kinase activity;

mediators, e.g. inhibitors, of PDGF receptor tyrosine kinase activity, e.g. Gleevec (imatinib);

mediators, e.g. inhibitors, of p38 MAP kinase activity, mediators, e.g. inhibitors, of VEGF receptor tyrosine kinase activity, mediators, e.g. inhibitors, of PKC activity, e.g. as disclosed in WO0238561 or WO0382859, e.g. the compound of Example 56 or 70;

mediators, e.g. inhibitors, of JAK3 kinase activity, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO2004052359 or WO2005066156;

mediators, e.g. agonists or modulators of S1P receptor activity, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts;

immunosuppressive monoclonal antibodies, e.g., monoclonal antibodies to leukocyte receptors, e.g., Blys/BAFF receptor, MHC, CD2, CD3, CD4, CD7, CD8, CD25, CD28, CD40, CD45, CD52, CD58, CD80, CD86, IL-12 receptor, IL-17 receptor, IL-23 receptor or their ligands;

other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y;

mediators, e.g. inhibitors of adhesion molecule activities, e.g. LFA-1 antagonists, ICAM-1 or -3 antagonists, VCAM-4 antagonists or VLA-4 antagonists, mediators, e.g. antagonists of CCR9 activity, mediators, e.g. inhibitors, of MIF activity, which are different from the compounds of the present invention, e.g. including other low molecular compounds or antibodies, 5-aminosalicylate (5-ASA) agents, such as sulfasalazine, Azulfidine®, Asacol®, Dipentum®, Pentasa®, Rowasa®, Canasa®, Colazal®, e.g. drugs containing mesalamine; e.g mesalazine in combination with heparin;

mediators, e.g. inhibitors, of TNF-alpha activity, e.g. including antibodies which bind to TNF-alpha, e.g. infliximab (Remicade®), nitric oxide releasing non-steriodal anti-inflammatory drugs (NSAIDs), e.g. including COX-inhibiting NO-donating drugs (CINOD);

phosphordiesterase, e.g. mediators, e.g. inhibitors of PDE4B activity, mediators, e.g. inhibitors, of caspase activity, 'multi-functional anti-inflammatory' drugs (MFAIDs), e.g. cytosolic phoshpholipase A2 (cPLA2) inhibitors, such as membrane-anchored phospholipase A2 inhibitors linked to glycosaminoglycans;

antibiotics, such as penicillins, cephalosporins, erythromycins, tetracyclines, sulfonamides, such as sulfadiazine, sulfisoxazole; sulfones, such as dapsone; pleuromutilins, fluoroquinolones, e.g. metronidazole, quinolones such as ciprofloxacin; levofloxacin; probiotics and commensal bacteria e.g. Lactobacillus, Lactobacillus reuteri;

antiviral drugs, such as ribivirin, vidarabine, acyclovir, ganciclovir, zanamivir, oseltamivir phosphate, famciclovir, atazanavir, amantadine, didanosine, efavirenz, foscarnet, indinavir, lamivudine, nelfinavir, ritonavir, saquinavir, stavudine, valacyclovir, valganciclovir, zidovudine.

Anticancer drugs which are prone to be useful as a combination partner with a compound of the present invention e.g. include oxaliplatin, triciribine, permetrexed (Alimta®), sunitinib (SU11248), temozolidine, daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU) floxuridine (5-FUdR), methotrexate (MTX), colchicine, vincristine, vinblastine, etoposide, teniposide, cisplatin, diethylstilbestrol (DES), tipifarnib, bortezomib and drugs such as disclosed as "chemotherpeutic agents" in WO02066019, e.g. on pages 5 and 6 under i) to x), in more detail on pages 6 to 11, namely agents which are disclosed to be useful in combination treatment of solid tumors, Anesthetics which are prone to be useful as a combination partner with a compound of the present invention e.g. include ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine.

In the following examples which illustrate the invention references to temperature are in degrees Celsius (° C.).

The following abbreviations are used:
EX.: Example
EtOAc: ethyl acetate

RT: room temperature
EtOH: ethanol
m.p.: Melting point

EXAMPLE 1

3-Cyclohexyl-7-hydroxy-3,4-dihydro-benzo[e][1,3]oxazin-2-one of formula

A. 3-Cyclohexyl-7-methoxy-3,4-dihydro-benzo[e][1,3]oxazin-2-one 40 g of cyclohexylamine are added to a solution of 26 g of 2-hydroxy-4-methoxy-benzaldehyde in 800 ml of absolute EtOH at RT. The mixture obtained is stirred for 1.5 hours, cooled to 0°, and 20 g of $NaBH_4$ are added in portions. The mixture obtained is stirred for 3 hours at RT, poured into $H_2O$ and the mixture obtained is extracted with $CH_2Cl_2$. Two phases are formed and are separated. The organic layer obtained is dried, 42 g of carbonyl-diimidazole are added and the mixture obtained is stirred for 16 hours at RT. To the mixture obtained additional 21.5 g of carbonyl-diimidazole are added, the mixture obtained is stirred for 3 hours, washed with 1N HCl, a saturated, aqueous solution of $NaHCO_3$ and brine, dried and concentrated in vacuo. 3-Cyclohexyl-7-methoxy-3,4-dihydrobenzo[e][1,3]-oxazin-2-one is obtained. m.p.: 76-77°; $^1$H-NMR ($CDCl_3$): δ 6.99 (d, J=8.4 Hz, 1H), 6.66 (dd, J=2.5+8.4 Hz, 1H), 6.57 (d, J=2.5 Hz, 1H), 4.30 (s, 2H), 4.24 (tt, J=3.6+11.6 Hz, 1H); 3.78 (s, 3H), 1.33-1.90 (m, 9H), 1.02-1.20 (m, 1H).

A sample of the compound obtained according to a) is subjected to flash chromatography on silica gel and the fractions comprising purified 3-cyclohexyl-7-methoxy-3,4-dihydro-benzo[e][1,3]oxazin-2-one are treated with HCl. 3-cyclohexyl-7-methoxy-3,4-dihydro-benzo[e][1,3]oxazin-2-one in the form of a hydrochloride is obtained. m.p.: 169-172°, $^1$H-NMR ($CDCl_3$) δ 6.86 (d, J=8.25 Hz, 1H), 6.41 (d, J=2.55 Hz, 1H), 6.33 (dd, J=2.55+8.25 Hz, 1H), 3.96 (s, 2H), 3.76 (s, 3H), 2.53 (tt, J=3.7+10 Hz, 1H), 1.92-2.03 (m, 2H), 1.56-1.80 (m, 3H), 1.03-1.37 (m, 5H).

B. Production of 3-Cyclohexyl-7-hydroxy-3,4-dihydro-benzo[e][1,3]oxazin-2-one

A mixture of 66 g of 3-cyclohexyl-7-methoxy-3,4-dihydro-benzo[e][1,3]oxazin-2-one and 200 g of pyridinium HCl are heated without solvent on a metal bath to 220° C. for 45 minutes whilst stirring. Evolving HCl gas is sucked off. The mixture obtained is cooled to RT, the melt obtained is dissolved in $H_2O$ and EtOAc and two phases obtained are separated. The aqueous layer obtained is extracted with EtOAc and washed with 1N HCl, dried and concentrated in vacuo. The concentration residue obtained is filtered over silica gel and the filtration residue obtained is concentrated. 3-Cyclohexyl-7-hydroxy-3,4-dihydro-benzo[e][1,3]oxazin-2-one is obtained in crystallized form. m.p. 193-196°.

$^1$H-NMR ($CDCl_3$) δ 7.19 (br.s, 1H), 6.95 (d, J=8.3 Hz, 1H), 6.65 (dd, J=2.4+8.3 Hz, 1H), 4.30 (s, 2H), 4.23 (tt, J=3.6+11.6 Hz, 1H), 1.30-1.90 (m, 9H), 1.02-1.20 (m, 1H).

Analogously as set out in Example 1, but using appropriate starting materials, compounds of formula

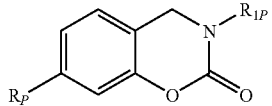

are obtained wherein $R_P$ is hydroxy and $R_{1P}$ is as set out in TABLE 1 having the melting point and/or $^1$H-NMR-data ($^1$H-NMR-data or $^{13}$C-NMR data are determined in CDCl$_3$, if not otherwise indicated) as set out in TABLE 1 below.

TABLE 1

| EX. | $R_{1P}$ | F.p./$^1$H-NMR |
|---|---|---|
| 1 | cyclohexyl-methyl | 193–196° |
| 2 | 4-methylphenyl-O-CH$_3$ | 212–215° |
| 3 | 4-methylcyclohexyl-OH | 239–247° |
| 4 | phenyl-methyl | 4.78 (s, 2H), 5.96–6.65 (m, 2H), 6.88–7.06 (m, 1H), 7.22–7.50 (m, 5H), 8.98 (bs, 1H) |
| 5 | 3-hydroxyphenyl-methyl | 226–228° |
| 6 | 4-hydroxyphenyl-methyl | 6.44 (d, 1H), 6.56 (dd, 1H), 6.74–6.82 (m, 2H), 7.03 (d, 1H), 7.20–7.26 (m, 2H), 9.58 (bs, 1H), 9.78 (bs, 1H) |

TABLE 1-continued

| EX. | $R_{1P}$ | F.p./$^1$H-NMR |
|---|---|---|
| 7 | 4-methylphenyl-O-S(=O)$_2$-NH$_2$ | 224–227° |
| 8 | 4-methylphenyl-O-Si(CH$_3$)$_2$-C(CH$_3$)$_3$ | 212–216° |
| 9 | benzo-crown ether with methyl | 167–169° |
| 10 | 2-ethylphenyl-methyl | 164–169° |

$^1$HNMR-data obtained for all compounds listed in TABLE 1 confirm their chemical structure Analogously to a method as described in Example 1, but using appropriate starting materials compounds of formula

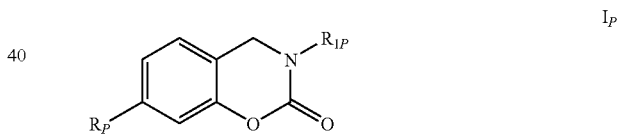

are obtained wherein $R_P$ and $R_{1P}$ are as defined in TABLE 2 below having the melting point as set out in TABLE 2 below.

TABLE 2

| EX. | $R_P$ | $R_{1P}$ | Fp. (° C.) |
|---|---|---|---|
| 11 | OH | 4-methylphenyl-OCF$_3$ | 204–208 |
| 12 | NH$_2$SO$_3$ | 3-methylphenyl-O-S(=O)$_2$-NH$_2$ | 90–99 |

TABLE 2-continued

| EX. | $R_P$ | $R_{1P}$ | Fp. (° C.) |
|---|---|---|---|
| 13 | H | 4-methoxyphenyl-methyl (p-tolyl with OCH₃) | 141-143 |
| 14 | NH₂SO₃ | cyclohexyl-methyl | 179-184 |
| 15 | NH₂SO₃ | 4-(sulfamoyloxy)phenyl-methyl | 53-55 |
| 16 | H | 4-biphenyl-methyl | 217-219 |
| 17 | NH₂SO₃ | 4-methoxyphenyl-methyl | 196-199 |
| 18 | NH₂SO₃ | phenyl-methyl (tolyl) | 197-199 |
| 19 | OH | n-hexyl | 108-111 |
| 20 | NH₂SO₃ | 4-hydroxyphenyl-methyl | 186-189 |
| 21 | OH | 1-naphthyl-methyl | 242-244 |
| 22 | H | 4-bromophenyl-methyl | 153-164 |

TABLE 2-continued

| EX. | $R_P$ | $R_{1P}$ | Fp. (° C.) |
|---|---|---|---|
| 23 | NH$_2$SO$_3$ | ethylphenyl | 176-179 |
| 24 | benzyl methyl ether | methyl 4-methylbenzoate | 184-188 |
| 25 | CH$_3$O | 4-methylphenyl sulfamate | 197-209 |
| 26 | CH$_3$O | 4-methylphenol | 242-250 |
| 27 | F | 4-methoxy-methylbenzene | 164-166 |
| 28 | F | 3-methoxy-methylbenzene | 130-132 |
| 29 | H | 3-methyl-phenyl benzyl ether | 146-150 |
| 30 | H | ethyl 1-(1-phenylethyl)-4-methylpiperidine-2-carboxylate | |

[1] HNMR-data obtained for all compounds listed in TABLE 2 confirm their chemical structure

What is claimed is:

1. A compound of formula

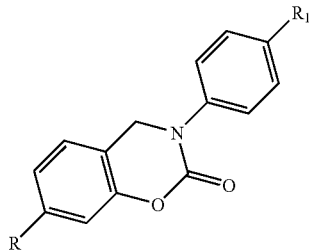

and salts thereof, wherein

R is hydroxy or $OR_2$ $R_1$ is hydrogen, halogen, hydroxy, $NH_2SO_2$, $(C_{1-4})$alkoxy, halo$(C_{1-4})$alkoxy, tri$(C_{1-6}$alkylsilyloxy and $(C_{1-4})$alkoxycarbonyl, and $R_2$ is $(C_{1-4})$alkyl, halo$(C_{1-4})$alkyl, $(C_{6-18})$aryl$(C_{1-4})$alkyl or $NH_2SO_3$.

2. A compound according to claim 1 of formula

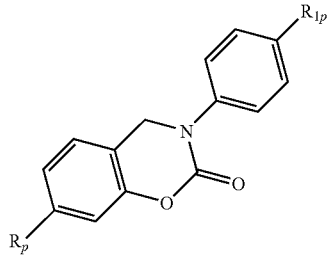

wherein $R_p$ is hydroxy, aminosulfonyloxy, methoxy, or benzyloxy, and $R_{1p}$ is halogen, hydroxy, $NH_2SO_2$, $(C_{1-4})$alkoxy, halo$(C_{1-4})$alkoxy, tri$(C_{1-6})$alkylsilyloxy and $(C_{1-4})$alkoxycarbonyl.

3. A compound according to claim 1 of formula

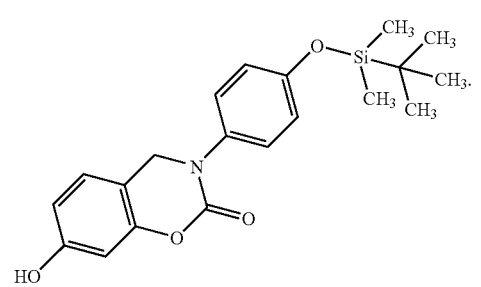

4. A compound according to claim 1 of formula

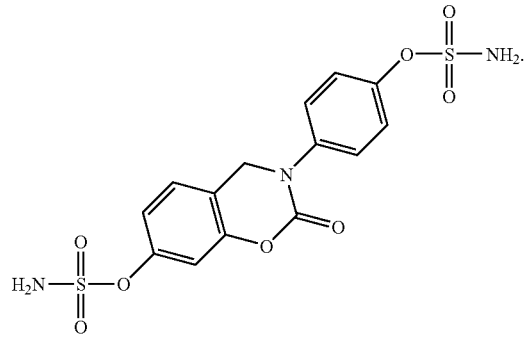

5. A compound of claim 1 in the form of a salt.

6. A pharmaceutical composition comprising a compound of claim 1 in association with at least one pharmaceutical excipient.

* * * * *